(12) United States Patent
Hilden et al.

(10) Patent No.: US 7,858,777 B2
(45) Date of Patent: Dec. 28, 2010

(54) PREPARATION METHOD FOR QUETIAPINE

(75) Inventors: Leif Hilden, Kauniainen (FI); Arne Grumann, Kauniainen (FI); Soini Huhta, Espoo (FI); Petteri Rummakko, Espoo (FI)

(73) Assignee: Fermion Oy, Espoo (FI)

( * ) Notice: Subject to any disclaimer, the term of this patent is extended or adjusted under 35 U.S.C. 154(b) by 1025 days.

(21) Appl. No.: 10/572,370

(22) PCT Filed: Sep. 23, 2004

(86) PCT No.: PCT/FI2004/000561

§ 371 (c)(1),
(2), (4) Date: Jan. 8, 2007

(87) PCT Pub. No.: WO2005/028459

PCT Pub. Date: Mar. 31, 2005

(65) Prior Publication Data

US 2007/0111986 A1    May 17, 2007

Related U.S. Application Data

(60) Provisional application No. 60/504,982, filed on Sep. 23, 2003.

(51) Int. Cl.
*C07D 295/20*    (2006.01)
*C07D 281/16*    (2006.01)

(52) U.S. Cl. ..................................................... 540/551
(58) Field of Classification Search .................. 540/551
See application file for complete search history.

(56) References Cited

U.S. PATENT DOCUMENTS

| 3,539,573 A | 11/1970 | Schmutz et al. |
| 2007/0111987 A1 | 5/2007 | Rummakko et al. |

FOREIGN PATENT DOCUMENTS

| EP | 0 240 228 A1 | 10/1987 |
| EP | 0 282 236 A1 | 9/1988 |
| WO | WO-01/55125 A | 8/2001 |

OTHER PUBLICATIONS

Warawa et al., Journal of Medicinal Chemistry, American Chemical Society, Washington, US, vol. 44, Feb. 1, 2001, pp. 372-389.

*Primary Examiner*—Brenda L Coleman
(74) *Attorney, Agent, or Firm*—Birch, Stewart, Kolasch & Birch, LLP

(57) ABSTRACT

The present invention discloses a process for the preparation of quetiapine, which comprises the ring closure and deprotection of a compound of the formula (I), as well as novel intermediates in the process.

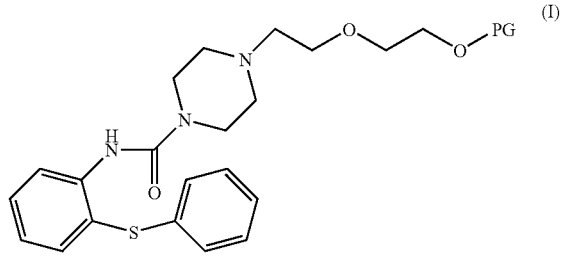

4 Claims, No Drawings

PREPARATION METHOD FOR QUETIAPINE

This application is the National Phase of PCT application PCT/FI2004/000561, filed Sep. 23, 2004 and claims priority under 35 U.S.C. 119(e) on U.S. Provisional Application No. 60/504,982, filed Sep. 23, 2003, of which are hereby incorporated by reference.

FIELD OF THE INVENTION 11-(4-[2-(2-hydroxyethoxy)ethyl]-1-piperazinyl]dibenzo[b,f]-1,4-thiazepine (1) is a well established drug substance known under the INN name quetiapine.

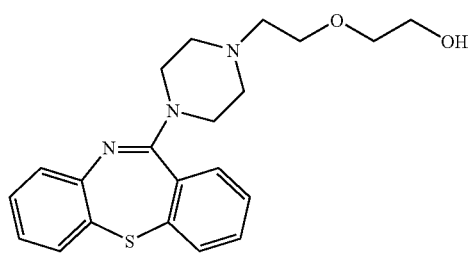

I

It is used as an antipsychotic or neuroleptic. The present invention provides an economical alternative method for the preparation of quetiapine in high yield and purity. Further objects of the invention are novel intermediates useful in the process according to the invention.

BACKGROUND OF THE INVENTION

Several methods for the preparation of quetiapine are known, as disclosed in e.g. GB 8607684, GB 8705574, and WO 01/55125. The known methods involve reacting a halo derivative (e.g. iminochloride) of dibenzo[b,f][1,4]-thiazepin-11(10-H)-one with 1-[2-(hydroxyethoxy)-ethyl]piperazine; reacting the aforementioned halo derivative with piperazine and reacting the resulting intermediate with a haloethoxyethanol; and reacting a haloethylpiperazinylthiazepine derivative with ethylene glycol.

SUMMARY OF THE INVENTION

According to the present invention, the target compound I is obtained by cyclizing a compound of formula II

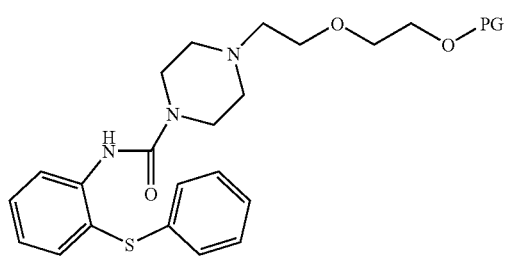

II wherein PG represents a protective group, and subsequently removing the protective group.

The compound of formula II is prepared either a) by attaching the protective group PG to the hydroxyl group of compound III

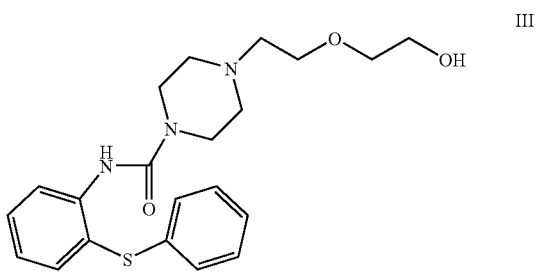

III which may be prepared by a one pot reaction involving 2-phenylsulfanylphenylamine, 1-[2-(hydroxyethoxy)-ethyl]piperazine and a coupling agent e.g. phosgene or equivalent; or b) by attaching the protective group to the hydroxyl group of 1-[2-(hydroxyethoxy)-ethyl]piperazine prior to reaction with 2-phenylsulfanylphenylamine and the coupling agent.

Further objects of the invention are the novel intermediates III, IV and V:

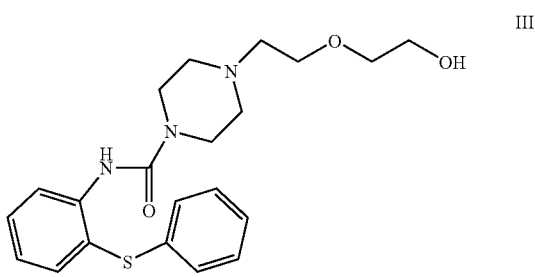

III

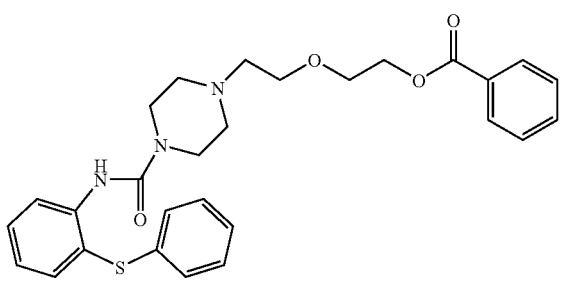

IV

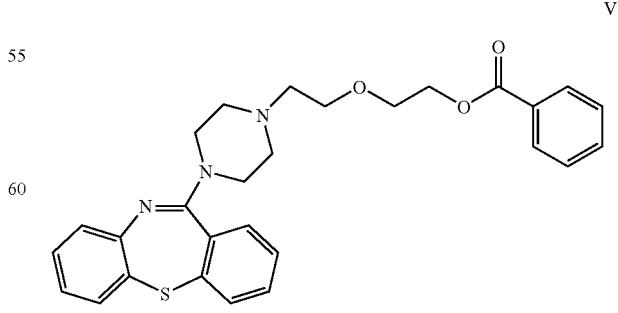

V

DISCLOSURE OF THE INVENTION 2-phenylsulfanylphenylamine may be prepared e.g. by reacting 1-chloro-2-nitrobenzene with benzenethiol and catalytically reducing the nitro group, e.g. as disclosed in the literature. According to the method of the present invention, compound III or IV is obtained without isolation of intermediates by allowing 2-phenylsulfanylphenylamine to react with a carbonyl compound VI

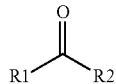

VI wherein R1 and R2 may independently be halo, p-nitrophenyl, imidazolyl or —OR wherein R is alkyl or aryl, and adding 1-[2-(hydroxyethoxy)-ethyl]piperazine either as such or with a protective group on the hydroxy group. Preferred carbonyl compounds VI include phosgene, diphosgene, triphosgene, (p-nitro)phenylchloroformate, methylchloroformate, dimethyl carbonate and carbonyldi-imidazole. Preferred protective groups inlude ethers and esters, e.g. benzoyl, acetyl, benzyl and tetrahydropyryl.

The reaction of 2-phenylsulfanylphenylamine with the compound of formula VI is preferably carried out in a suitable solvent; preferably toluene, but other aromatic and aliphatic hydrocarbons, also chlorinated derivatives, may be used. The reaction temperature may range from −50° C. to 25° C. The subsequent reaction with protected or unprotected 1-[2-(hydroxyethoxy)-ethyl]piperazine is preferably carried out at −10° C. to 25° C. in the presence of a base, preferably triethylamine but other bases, e.g. other tertiary amines, may be used.

In the case 1-[2-(hydroxyethoxy)-ethyl]piperazine is used in the above step without a protective group, the protective group PG is subsequently introduced to yield compound II. Preferably, benzoyl chloride is used; other alternatives include acid chlorides and anhydrides, as well as ether-forming reagents. The reaction is preferably carried out at a temperature of 0-100° C., preferably at ambient temperature.

Compound II is cyclized by treatment with a ring closure agent. Such agents include phosphorus oxychloride, phosphorus pentoxide and polyphosphoric acid. An advantageous reagent is a mixture of phosphorus oxychloride and phosphorus pentoxide, preferably using an excess of phosphorus oxychloride as a solvent.

Possible co-solvents are aliphatic or aromatic hydrocarbons, preferably toluene, as well as chlorinated hydrocarbons. The preferable temperature ranges from 50 to 130° C., preferably about 80-100° C.

Following cyclization, the protective group on the hydroxyl moiety is removed to produce the target compound I, which can be further transferred to a pharmaceutically acceptable salt thereof. If the protective group is susceptible to hydrolysis in basic conditions, sodium hydroxide in ethanol at 20-100° C. is preferably used.

EXAMPLES

Example 1

4-[2-(2-hydroxyethoxy)-ethyl]-piperazine-carboxylic acid (2-phenylsulfanyl-phenyl)-amide The reaction was carried out without isolation of intermediates in a one pot synthesis. Toluene (30 ml) and phosgene solution (20% in xylene, 9.1 ml, 17.16 mmol) were charged into a reaction flask. The mixture was cooled to −50° C. A mixture of 2-phenylsulfanylphenylamine (3 g, 14.9 mmol), triethylamine (2.4 ml, 17.1 mmol) and toluene (5 ml) was charged into the reaction flask at −50° C. during 5 min. The mixture was allowed to reach room temperature and it was stirred at room temperature for 1.5 h. Then the reaction mixture was added to another reaction flask at −10-0° C., containing the cooled mixture of 1-[2-(hydroxyethoxy)-ethyl]-piperazine, triethylamine (2.7 ml) and toluene (20 ml). The reaction mixture was stirred at room temperature for 1.5 h. Precipitated triethylamine hydrochloride was filtered off. The resulting toluene solution was washed twice with saturated NaCl-water (10 ml), dried with $K_2CO_3$ and evaporated in vacuo. The yield of 4-[2-(2-hydroxyethoxy)-ethyl]-piperazine-carboxylic acid (2-phenylsulfanyl-phenyl)-amide was 4.76 g.

$^1$H NMR ($CDCl_3$). 2.35 (4H, m), 2.53 (2H, t), 3.34 (4H, t), 3.60 (4H, m), 3.67 (2H, t), 7.0-7.63 (9H, m). $^{13}$C NMR ($CDCl_3$). 43.5, 52.8, 57.7, 61.8, 67.7, 72.4, 115.3, 118.4, 122.8, 125.4, 126.1, 126.3, 126.4, 127.8, 128.9, 129.2, 131.2, 141.2, 153.9

Example 2

Benzoic acid 2-{2-[4-(2-phenylsulfanyl-phenylcarbamoyl)piperazin-1-yl]-ethoxy}-ethyl ester 4-[2-(2-hydroxyethoxy)-ethyl]-piperazine-carboxylic acid (2-phenylsulfanyl-phenyl)-amide (4 g, 10 mmol), triethylamine (2 ml, 15 mmol) and toluene (50 ml) were charged into a reaction flask. Benzoyl chloride (1.7 g, 12 mmol) in toluene (5 ml) was added at 0-10° C. The mixture was stirred for 16 h at 20° C. Cold water (50 ml) and 1 M NaOH (100 ml) were added. The mixture was stirred for 20 min. The water phase was separated. The organic phase was washed with saturated NaCl solution (25 ml) and evaporated in vacuo. The yield of benzoic acid 2-{2-[4-(2-phenylsulfanyl-phenylcarbamoyl)piperazin-1-yl]-ethoxy}-ethyl ester was 4.91 g.

$^1$H NMR ($CDCl_3$). 2.35 (4H, m), 2.54 (2H, m), 3.28 (4H, m), 3.63 (2H, m), 3.77 (2H, m), 4.47 (2, m), 7.0-8.3 (14H, m). $^{13}$C NMR ($CDCl_3$). 43.7, 53.0, 57.6, 63.9, 68.9, 69.0, 118.4, 119.8, 122.7, 126.5, 127.1, 129.2, 129.3, 129.6, 130.0, 131.0, 133.1, 135.6, 136.0, 136.5, 140.1, 141.3, 154.0, 166.4

Example 3

Benzoic acid 2-[2-(4-dibenzo[b,f][1,4]-thiazepin-11-yl-piperazin-1-yl]-ethoxy]-ethyl ester Benzoic acid 2-{2-[4-(2-phenylsulfanyl-phenylcarbamoyl)piperazin-1-yl]-ethoxy}-ethyl ester (2 g, 3.96 mmol), phosphorus oxychloride (15 ml) and phosphorus pentoxide (2 g) were charged into a reaction flask. Then the mixture was stirred at 90° C. for 19 h. Phosphorus oxychloride was evaporated in vacuo. Dichloromethane (20 ml) and ice-water (20 ml) were added to the residue. $NaHCO_3$ was added until the pH was 7-8. The organic phase was separated, washed with saturated NaCl-water (10 ml), dried with $Na_2SO_4$ and evaporated in vacuo. Yield of benzoic acid 2-[2-(4-dibenzo[b,f][1,4]-thiazepin-11-yl-piperazin-1-yl]-ethoxy]-ethyl ester 1.53 g.

$^1$H NMR ($CDCl_3$). 2.52-2.67 (6H, m), 3.67-3.80 (8H, m), 4.47 (2H, m), 6.90-8.0 (13H, m). $^{13}$C NMR ($CDCl_3$). 46.1, 53.4, 63.7, 68.9, 69.0, 69.1, 122.7, 125.4, 127.1, 128.2, 128.4, 129.0, 129.1, 129.2, 129.6, 129.7, 130.0, 130.7, 131.1, 132.1, 133.0, 134.1, 139.8, 160.7, 166.5

Example 4

Quetiapine

Benzoic acid 2-[2-(4-dibenzo[b,f][1,4]-thiazepin-11-yl-piperazin-1-yl]-ethoxy]-ethyl ester (1.5 g, 2.97 mmol), ethanol (10 ml) and 50% NaOH (1 ml) were charged into a reaction flask. Then the mixture was stirred at 80° C. for 2 h. The reaction mixture was evaporated in vacuo. Ethyl acetate (20 ml) and saturated NaCl-water (15 ml) were added to the residue. The water phase was separated. To the organic phase was added 1 M HCl (10 ml). To the combined water phase was added 50% NaOH until the pH was 12 and saturated NaCl-water (10 ml). The alkaline water phase was extracted twice with ethyl acetate (10 ml). The combined organic phase was washed with saturated NaCl-water (10 ml), dried with Na$_2$SO$_4$ and evaporated. Yield of quetiapine 0.93 g.

What is claimed is:

1. A method for the preparation of the compound of formula I:

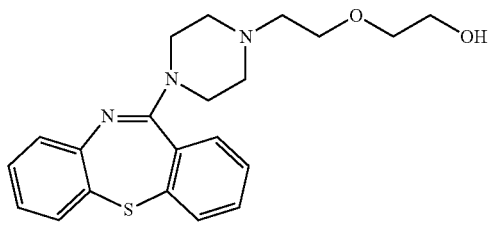
I said method comprising treating a compound of the formula II:

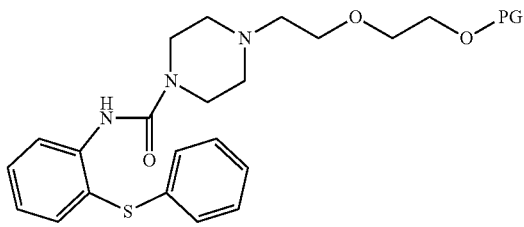
II wherein PG is a protective group, with a ring closure agent to produce a compound of formula VII:

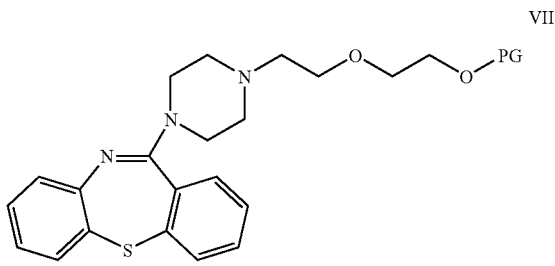
VII and removing the protective group to produce the compound of formula I.

2. The method of claim 1, wherein PG is benzoyl.

3. The method of claim 1, wherein the ring closure agent is a mixture of phosphorus oxychloride and phosphorus pentoxide.

4. The method of claim 1, wherein the compound of formula II is prepared by reaction between 2-phenylsulfanylphenylamine, a compound of formula VI:

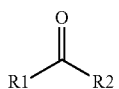
VI wherein R1 and R2 may independently be halo, p-nitrophenyl, imidazolyl or —OR wherein R is alkyl or aryl; and either a) or b):

a) 1-[2-(hydroxyethoxy)-ethyl]piperazine, whereby the protective group PG in formula II is subsequently attached;

b) an O-protected 1-[2 (hydroxyethoxy)-ethyl]piperazine.

\* \* \* \* \*